United States Patent
Liboff

(10) Patent No.: US 10,625,089 B1
(45) Date of Patent: Apr. 21, 2020

(54) SYSTEM FOR TREATMENT OF ALZHEIMER'S DISEASE USING MAGNETIC FIELDS

(71) Applicant: Abraham Liboff, Delray Beach, FL (US)

(72) Inventor: Abraham Liboff, Delray Beach, FL (US)

( * ) Notice: Subject to any disclaimer, the term of this patent is extended or adjusted under 35 U.S.C. 154(b) by 0 days.

(21) Appl. No.: 16/542,028

(22) Filed: Aug. 15, 2019

(51) Int. Cl.
*A61N 2/00* (2006.01)
*A61N 2/02* (2006.01)
*A61B 5/00* (2006.01)

(52) U.S. Cl.
CPC ............ *A61N 2/006* (2013.01); *A61B 5/4088* (2013.01); *A61B 5/6892* (2013.01); *A61N 2/02* (2013.01); *A61N 2/002* (2013.01)

(58) Field of Classification Search
CPC .............. A61N 2/02; A61N 2/00; A61N 2/004
USPC ........................................................ 600/9–15
See application file for complete search history.

(56) References Cited

U.S. PATENT DOCUMENTS

| 5,045,050 A * | 9/1991 | Liboff | A61N 2/02 600/14 |
|---|---|---|---|
| 2003/0045770 A1* | 3/2003 | van Mullekom | A61N 2/02 600/9 |
| 2018/0154105 A1* | 6/2018 | Bode | A61M 21/02 |

* cited by examiner

*Primary Examiner* — Samuel G Gilbert
(74) *Attorney, Agent, or Firm* — Mark Terry

(57) ABSTRACT

A method and system for treating Alzheimer's disease in a patient is provided. The system includes a magnetometer configured for measuring a directional component of a local magnetic field located in a vicinity of the patient's head, thereby producing a measurement B, a mat such that the patient may rest his head on said mat, the mat comprising coils that produce a uniform magnetic field emanating perpendicularly to a plane of the mat, a current generator for generating and transmitting a current to the coils of the mat, and a computing system for: receiving the measurement B, calculating a frequency f of a current necessary for the coils to produce ion cyclotron resonance of amyloid beta, wherein the following formula is used to calculate said frequency f: $f=(1/2\pi)(qB/m)$, where q/m is a charge to mass ratio of amyloid beta, and generating said current.

19 Claims, 4 Drawing Sheets

SYSTEM FOR TREATMENT OF ALZHEIMER'S DISEASE USING MAGNETIC FIELDS

CROSS-REFERENCE TO RELATED APPLICATIONS

This patent application claims priority to Italian patent application number 102018000006819 filed on Jun. 29, 2018. The subject matter of Italian patent application number 102018000006819 is hereby incorporated by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The technical field relates generally to computer or information security and, more specifically, to processes for improving the verification of identification and presence.

BACKGROUND

Alzheimer's disease is a progressive disease resulting in senile dementia. Broadly speaking, the disease falls into two categories: late onset, which occurs in old age (65+ years) and early onset, which develops well before the senile period, i.e., between 35 and 60 years. In both types of the disease, the abnormalities tend to be more severe and widespread in cases beginning at an earlier age. Alzheimer's disease is characterized by at least two types of lesions in the brain, senile plaques and neurofibrillary tangles. Senile plaques are areas of disorganized neuropil up to 150 μm across with extracellular amyloid deposits at the center visible by microscopic analysis of sections of brain tissue. Neurofibrillary tangles are intracellular deposits of microtubule associated with tau protein consisting of two filaments twisted about each other in pairs.

The principal constituent of the plaques is a peptide termed amyloid beta (Aβ) or β-amyloid peptide. Aβ peptide is an internal fragment of 39-43 amino acids of a precursor protein termed amyloid precursor protein (APP). Several mutations within the APP protein have been correlated with the presence of Alzheimer's disease. Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PS1 and PS2, are thought indirectly to affect processing of APP to generate increased amounts of long form Aβ. These observations indicate that Aβ, and particularly its long form, is a causative element in Alzheimer's disease.

One approach to treatment of Alzheimer's disease is the use of orally administered drugs. A problem with orally administered Alzheimer's drugs or nonsteroidal anti-inflammatory drugs is unpleasant side effects including severe nausea and gastric ulcers which patients develop following chronic use. Further, with chronic oral therapy the therapeutic value diminishes over time requiring dose escalation. In addition, limited transport of Alzheimer's drugs or other nonsteroidal anti-inflammatory drugs across the blood brain barrier increases the potential for systemic adverse side-effects. In order to maintain the same therapeutic affect with disease progression, the dose of Alzheimer's drugs taken orally must increase. In patients having adverse side-effects, treatment escalation is not possible. Thus, oral administration of Alzheimer's drugs is inherently dose-limiting. In addition to the problems just mentioned with orally administered Alzheimer's drugs or similar nonsteroidal anti-inflammatory drugs, the amount of drug entering the patient's blood system is minimized by uptake of the drugs by the gastrointestinal system.

Therefore, a need exists for improvements over the prior art, and more particularly for improved methods and systems for treating Alzheimer's disease.

SUMMARY

A method and system for treating Alzheimer's disease in a patient is provided. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, the system includes a magnetometer configured for measuring a directional component of a local magnetic field located in a vicinity of the patient's head, thereby producing a measurement B; a mat configured such that the patient may rest his head on said mat, the mat comprising a plurality of coils that, when activated, produce a uniform magnetic field emanating perpendicularly to a plane of the mat; a current generator coupled to the mat and configured for generating and transmitting a current to the plurality of coils of the mat; and a computing system coupled to the magnetometer and the current generator, the computing system configured for: 1) receiving the measurement B from the magnetometer; 2) calculating a frequency f of a current necessary for the plurality of coils of the mat to produce ion cyclotron resonance (ICR) of amyloid beta, wherein the following formula is used to calculate said frequency f: $f=(1/2\pi)(qB/m)$, where q/m is a charge to mass ratio of amyloid beta; and 3) generating a current with the frequency f, and transmitting said current to the plurality of coils of the mat.

BRIEF DESCRIPTION OF THE DRAWINGS

The accompanying drawings, which are incorporated in and constitute a part of this disclosure, illustrate various example embodiments. In the drawings.

DETAILED DESCRIPTION

Figure 1:
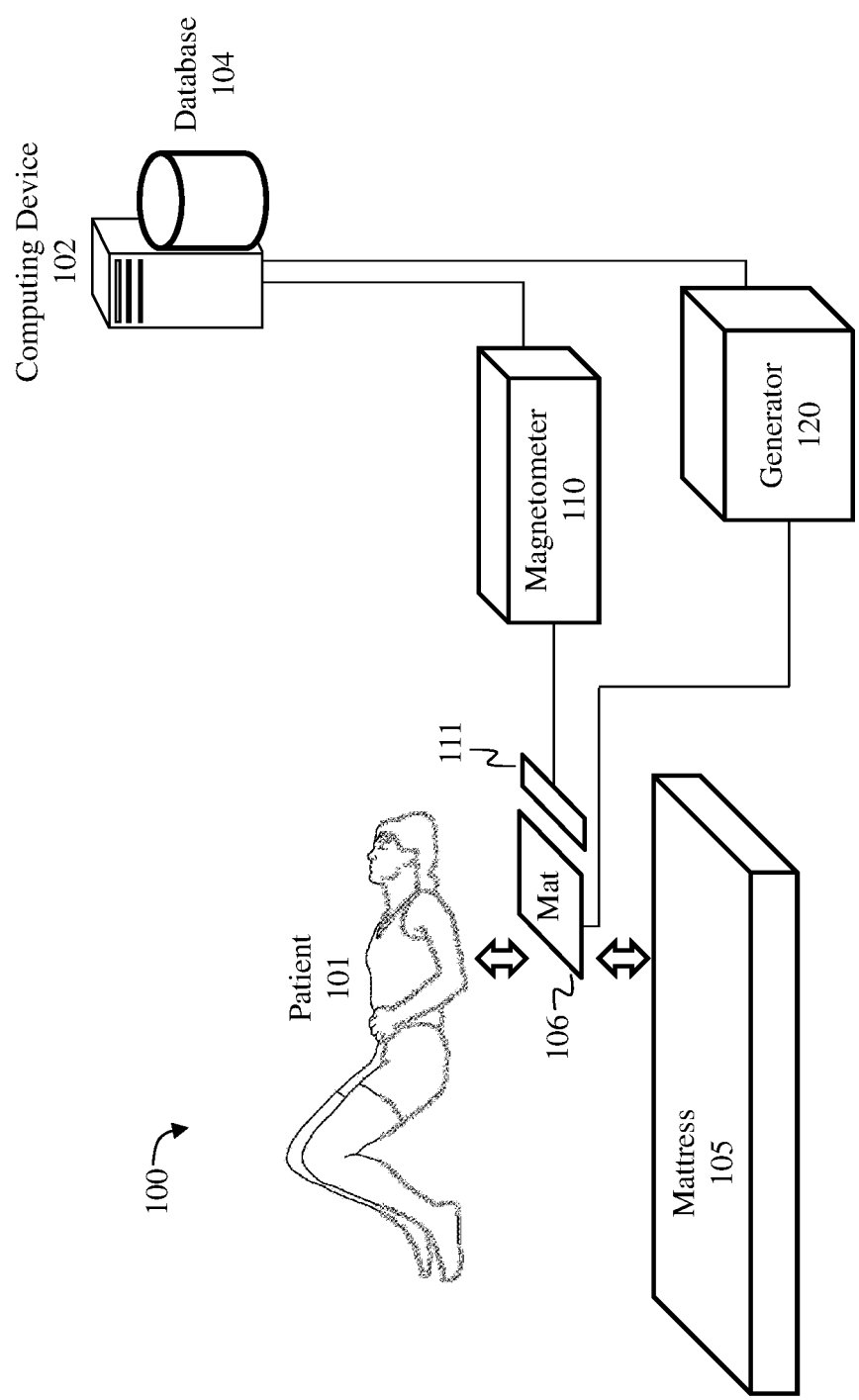
FIG. 1 is a diagram of an operating environment that supports a method and system for treating Alzheimer's disease in a patient, according to an example embodiment.

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the claimed subject matter. Instead, the proper scope of the claimed subject matter is defined by the appended claims.

The claimed subject matter improves over the prior art by providing a simple, cost-effective and user-friendly method for treating Alzheimer's disease in patients. The claimed subject matter provides a small and easy-to-operate device that can be used in homes, clinics and hospitals to treat Alzheimer's disease in a quick and non-invasive way. Also, the claimed subject matter does not require internal medicine, drugs, pharmaceuticals or other medicine to operate fully. Therefore, the claimed subject matter reduces or eliminates opportunities the problem with orally administered Alzheimer's drugs or nonsteroidal anti-inflammatory drugs, such as unpleasant side effects, dose escalation, treatment escalation and resulting problems with the patient's gastrointestinal system.

FIG. 1 is a diagram of an operating environment that supports a method and system 100 for treating Alzheimer's disease in a patient, according to an example embodiment. The system 100 includes a mattress 105, which may be a large pad for supporting the reclining body, used as or on a bed, consisting of a quilted or similarly fastened case, usually of heavy cloth, that contains hair, straw, cotton, foam rubber, etc., or a framework of metal springs. The system 100 may also include a mat 106 configured for placement on a horizontal surface (i.e., the mattress 105) such that the patient 101 may rest his head on said mat, the mat comprising a plurality of coils that, when activated, produce a uniform magnetic field emanating perpendicularly to a plane of the mat 106. The mat 106 may comprise a first planar element including a foam-based material with elastic characteristics, wherein the plurality of coils are located underneath the first planar element. This provides a comfortable surface for the patient's head while still providing the coils necessary for the claimed subject matter to operate.

The system 100 also includes a magnetometer 110, which is an instrument that measures magnetism, including the direction, strength, or relative change of a magnetic field at a particular location. The magnetometer 110 may be a vector magnetometer that measures the vector components of a magnetic field. The magnetometer 110 may also be a total field magnetometer or scalar magnetometer that measures the magnitude of the vector magnetic field. The magnetometer 110 may also be an absolute magnetometer that measures the absolute magnitude or vector magnetic field, using an internal calibration or known physical constants of the magnetic sensor. The magnetometer 110 may also be a relative magnetometer that measures the magnitude or the vector magnetic field relative to a fixed but uncalibrated baseline. The magnetometer 110 may also be a portable or mobile magnetometer that may be manually carried or transported in a moving vehicle.

The magnetometer 110 may be configured for measuring a vertical component of a local magnetic field located in a vicinity of the patient's head, thereby producing a measurement B that represents said local magnetic field. FIG. 1 also shows a sensor 111 of the magnetometer that is used to measure a vertical component of the local magnetic field located in the vicinity of the patient's head.

The system 100 also includes a current generator coupled to the mat 106 and configured for generating and transmitting a current to the plurality of coils of the mat 106. The current generator generates and transmits an alternating current or a direct current to the plurality of coils of the mat 106. The current generator is an electronic circuit that delivers an electric current according to a selected frequency, amplitude, phase, wavelength, voltage and amperage.

The system 100 also includes a server or computing device 102 may be communicatively coupled with the magnetometer 110 and current generator 120, according to an example embodiment. Device 102 may comprise a cellular/mobile telephone, smart phone, tablet computer, laptop computer, handheld computer, desktop computer, wearable computer, or the like. Device 102 may also comprise other computing devices such as desktop computers, workstations, servers, and game consoles, for example. The device 102 may be connected either wirelessly or in a wired or fiber optic form to a communications network. Communications network may be a packet switched network, such as the Internet, or any local area network, wide area network, enterprise private network, cellular network, phone network, mobile communications network, or any combination of the above.

In one embodiment, the device 102 is configured for: 1) receiving the measurement B from the magnetometer; 2) calculating a frequency f of a current necessary for the plurality of coils of the mat to: i) produce ion cyclotron resonance (ICR) of cations related to Alzheimer's disease, and ii) produce a magnetic field with an intensity equal to or less than one microTesla, wherein the following formula is used to calculate said frequency f:

$$f=(1/2\pi)(qB/m), \text{ where } q/m \text{ is a charge to mass ratio of said cations;}$$

and 3) sending a command to the current generator 120 to product a current with the frequency f, and transmit said current to the plurality of coils of the mat 160. One of the cations related to Alzheimer's disease may include amyloid beta.

Computing device 102 includes a software engine that delivers applications, data, program code and other information to networked devices, such as 110, 120. The software engine of device 102 may perform other processes such as transferring multimedia data in a stream of packets that are interpreted and rendered by a software application as the packets arrive. FIG. 1 further shows that device 102 includes a database or repository 104, which may be a relational database comprising a Structured Query Language (SQL) database stored in a SQL server. The database 104 may serve user frequency data (located in database 104), which may be used by device 120.

Devices 102, 110, 120 may each include program logic comprising computer source code, scripting language code or interpreted language code that perform various functions of the disclosed embodiments. In one embodiment, the aforementioned program logic may comprise program module 407 in FIG. 4. It should be noted that although FIG. 1 shows only one computing device 102, the system of the disclosed embodiments supports any number of computing devices. Also note that although server 102 is shown as a single and independent entity, in one embodiment, server 102 and its functionality can be realized in a centralized fashion in one computer system or in a distributed fashion wherein different elements are spread across several interconnected computer systems.

Figure 2:
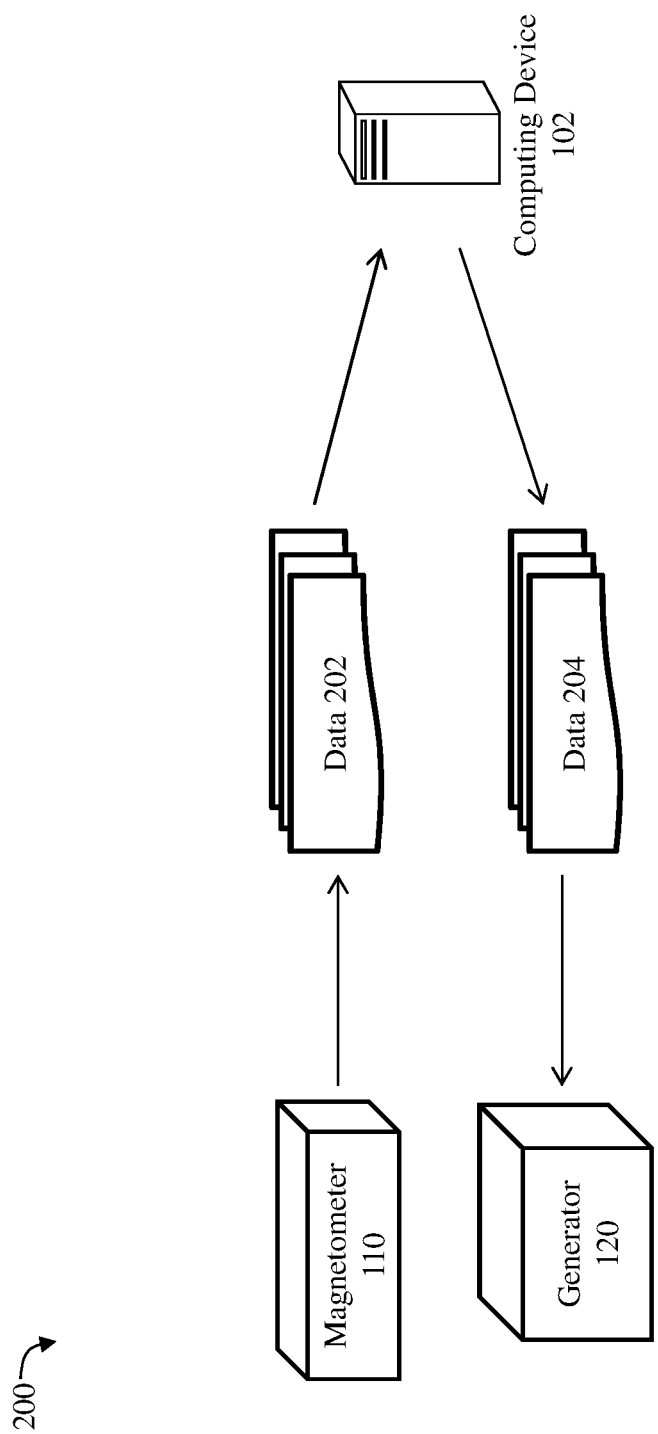
FIG. 2 is a diagram showing the data flow of a method and system for treating Alzheimer's disease in a patient, according to an example embodiment.
Figure 3:
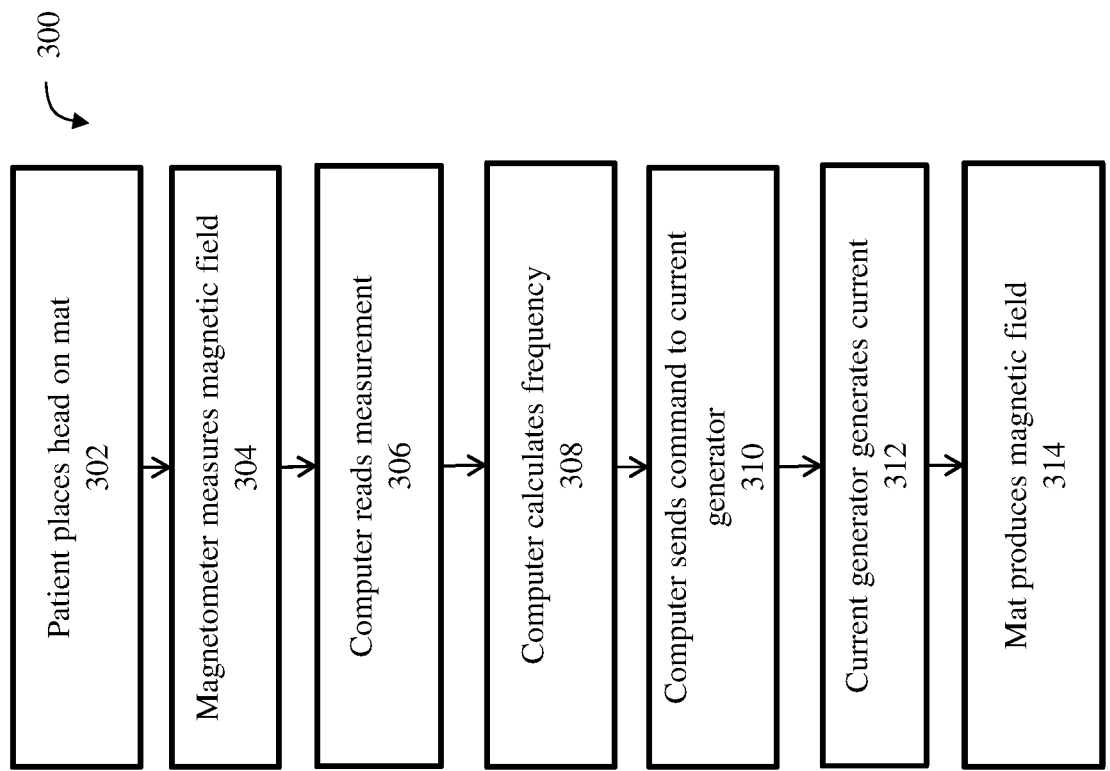
FIG. 3 is a flowchart showing the control flow of the method and system for treating Alzheimer's disease in a patient, according to an example embodiment.

The method and system for treating Alzheimer's disease in a patient 101 is described in more detail below, with reference to FIGS. 2, 3 and 4. The process of treating Alzheimer's disease in a patient 101 begins with step 302 of FIG. 3. In step 302, the user 111 lies on the mattress with his head on the mat 106. In step 304, the magnetometer 110 uses its sensor 111 to measure a vertical component of a local magnetic field located in a vicinity of the patient's head, thereby producing a measurement B that represents said local magnetic field. In step 306, the computing device 102 reads the measurement B as data 202. In step 308, the computing device 102 calculates a frequency f of a current necessary for the plurality of coils of the mat 106 to: i) produce ion cyclotron resonance (ICR) of cations related to Alzheimer's disease, and ii) produce a magnetic field with an intensity equal to or less than one microTesla, wherein the following formula is used to calculate said frequency f:

$f=(1/2\pi)(qB/m)$, where $q/m$ is a charge to mass ratio of said cations.

One of the cations related to Alzheimer's disease may include amyloid beta.

In step 310, the computing device 102 sends a command (including data 204) to the current generator 120 to produce a current with the frequency f, and transmit said current to the plurality of coils of the mat 160. In step 312, the current generator 120 produces a current with the frequency f, and transmits said current to the plurality of coils of the mat 160. In step 314, the plurality of coils of the mat 160 produce a magnetic field according to the current that was transmitted by the current generator, wherein the produced magnetic field affects the cations related to Alzheimer's disease.

Figure 4:
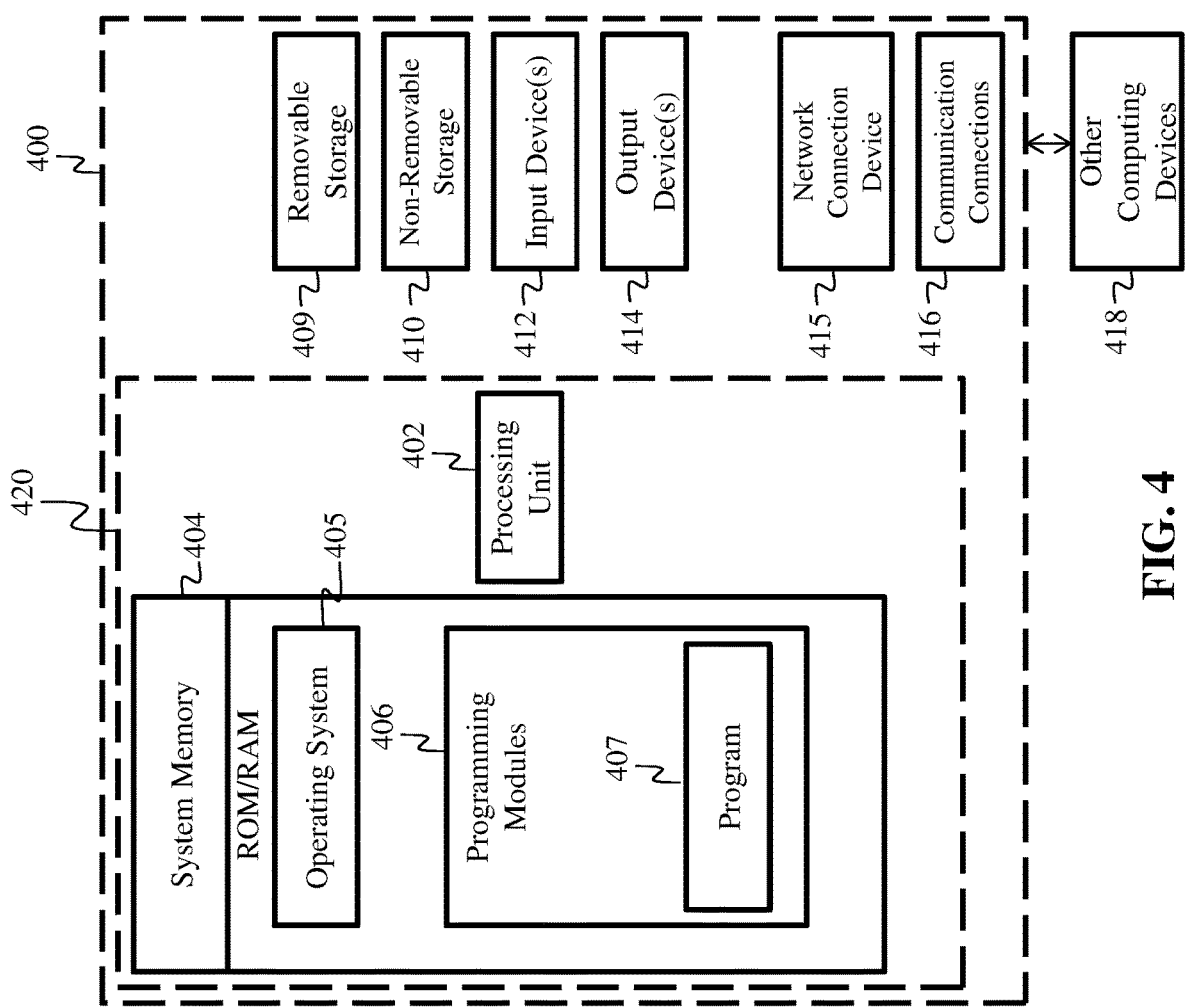
FIG. 4 is a block diagram of a computing device used with the example embodiments.

FIG. 4 is a block diagram of a system including an example computing device 400 and other computing devices. Consistent with the embodiments described herein, the aforementioned actions performed by devices 110, 120, 102 may be implemented in a computing device, such as the computing device 400 of FIG. 4. Any suitable combination of hardware, software, or firmware may be used to implement the computing device 400. The aforementioned system, device, and processors are examples and other systems, devices, and processors may comprise the aforementioned computing device. Furthermore, computing device 400 may comprise an operating environment for system 100 and processes 200, 300, as described above. Processes 200, 300 may operate in other environments and are not limited to computing device 400.

With reference to FIG. 4, a system consistent with an embodiment may include a plurality of computing devices, such as computing device 400. In a basic configuration, computing device 400 may include at least one processing unit 402 and a system memory 404. Depending on the configuration and type of computing device, system memory 404 may comprise, but is not limited to, volatile (e.g. random access memory (RAM)), non-volatile (e.g. read-only memory (ROM)), flash memory, or any combination or memory. System memory 404 may include operating system 405, and one or more programming modules 406. Operating system 405, for example, may be suitable for controlling computing device 400's operation. In one embodiment, programming modules 406 may include, for example, a program module 407 for executing the actions of devices 110, 120, 102. Furthermore, embodiments may be practiced in conjunction with a graphics library, other operating systems, or any other application program and is not limited to any particular application or system. This basic configuration is illustrated in FIG. 4 by those components within a dashed line 420.

Computing device 400 may have additional features or functionality. For example, computing device 400 may also include additional data storage devices (removable and/or non-removable) such as, for example, magnetic disks, optical disks, or tape. Such additional storage is illustrated in FIG. 4 by a removable storage 409 and a non-removable storage 410. Computer storage media may include volatile and nonvolatile, removable and non-removable media implemented in any method or technology for storage of information, such as computer readable instructions, data structures, program modules, or other data. System memory 404, removable storage 409, and non-removable storage 410 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 400. Any such computer storage media may be part of device 400. Computing device 400 may also have input device(s) 412 such as a keyboard, a mouse, a pen, a sound input device, a camera, a touch input device, etc. Output device(s) 414 such as a display, speakers, a printer, etc. may also be included. Computing device 400 may also include a vibration device capable of initiating a vibration in the device on command, such as a mechanical vibrator or a vibrating alert motor. The aforementioned devices are only examples, and other devices may be added or substituted.

Computing device 400 may also contain a network connection device 415 that may allow device 400 to communicate with other computing devices 418, such as over a network in a distributed computing environment, for example, an intranet or the Internet. Device 415 may be a wired or wireless network interface controller, a network interface card, a network interface device, a network adapter or a LAN adapter. Device 415 allows for a communication connection 416 for communicating with other computing devices 418. Communication connection 416 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 404, including operating system 405. While executing on processing unit 402, programming modules 406 (e.g. program module 407) may perform processes including, for example, one or more of the stages of the processes 200 and 300 as described above. The aforementioned processes are examples, and processing unit 402 may perform other processes. Other programming modules that may be used in accordance with embodiments herein may include electronic mail and contacts applications, word processing applications, spreadsheet applications, database applications, slide presentation applications, drawing or computer-aided application programs, etc.

Generally, consistent with embodiments herein, program modules may include routines, programs, components, data structures, and other types of structures that may perform particular tasks or that may implement particular abstract data types. Moreover, embodiments herein may be practiced with other computer system configurations, including handheld devices, multiprocessor systems, microprocessor-based or programmable consumer electronics, minicomputers, mainframe computers, and the like. Embodiments herein may also be practiced in distributed computing environments where tasks are performed by remote processing devices that are linked through a communications network. In a distributed computing environment, program modules may be located in both local and remote memory storage devices.

Furthermore, embodiments herein may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments herein may also be practiced using other technologies capable of performing logical operations such as, for example, AND, OR, and NOT, including but not limited to mechanical, optical, fluidic, and quantum technologies. In addition, embodiments herein may be practiced within a general purpose computer or in any other circuits or systems.

Embodiments herein, for example, are described above with reference to block diagrams and/or operational illustrations of methods, systems, and computer program products according to said embodiments. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments have been described, other embodiments may exist. Furthermore, although embodiments herein have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the claimed subject matter.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for treating Alzheimer's disease in a patient, comprising:
   a) a magnetometer configured for measuring a vertical component of a local magnetic field located in a vicinity of the patient's head, thereby producing a measurement B;
   b) a mat configured for placement on a horizontal surface such that the patient may rest his head on said mat, the mat comprising a plurality of coils that, when activated, produce a uniform magnetic field emanating perpendicularly to a plane of the mat;
   c) a current generator coupled to the mat and configured for generating and transmitting a current to the plurality of coils of the mat; and
   d) a computing system coupled to the magnetometer and the current generator, the computing system configured for:
      1) receiving the measurement B from the magnetometer;
      2) calculating a frequency f of a current necessary for the plurality of coils of the mat to: i) produce ion cyclotron resonance (ICR) of cations related to Alzheimer's disease, and ii) produce a magnetic field with an intensity equal to or less than one microTesla, wherein the following formula is used to calculate said frequency f:

$f=(½\pi)(qB/m)$, where $q/m$ is a charge to mass ratio of said cations;

3) generating a current with the frequency f, and transmitting said current to the plurality of coils of the mat.

2. The system of claim 1, wherein the magnetometer is a vector magnetometer.

3. The system of claim 1, wherein the magnetometer is a total field magnetometer.

4. The system of claim 1, wherein the mat comprises a first planar element including a foam-based material with elastic characteristics, wherein the plurality of coils are located underneath the first planar element.

5. The system of claim 1, wherein the current generator generates and transmits an alternating current to the plurality of coils of the mat.

6. The system of claim 1, wherein the current generator generates and transmits a direct current to the plurality of coils of the mat.

7. The system of claim 1, wherein one of the cations related to Alzheimer's disease include amyloid beta.

8. A system for treating Alzheimer's disease in a patient, comprising:
   a) a magnetometer configured for measuring a directional component of a local magnetic field located in a vicinity of the patient's head, thereby producing a measurement B;
   b) a mat configured such that the patient may rest his head on said mat, the mat comprising a plurality of coils that, when activated, produce a uniform magnetic field emanating perpendicularly to a plane of the mat;
   c) a current generator coupled to the mat and configured for generating and transmitting a current to the plurality of coils of the mat; and
   d) a computing system coupled to the magnetometer and the current generator, the computing system configured for:
      1) receiving the measurement B from the magnetometer;
      2) calculating a frequency f of a current necessary for the plurality of coils of the mat to: i) produce ion cyclotron resonance (ICR) of amyloid beta, and ii) produce a magnetic field with an intensity equal to or less than one microTesla, wherein the following formula is used to calculate said frequency f:

$f = (1/2\pi)(qB/m)$, where $q/m$ is a charge to mass ratio of amyloid beta;

3) generating a current with the frequency f, and transmitting said current to the plurality of coils of the mat.

9. The system of claim 8, wherein the magnetometer is a vector magnetometer.

10. The system of claim 8, wherein the magnetometer is a total field magnetometer.

11. The system of claim 8, wherein the mat comprises a first planar element including a foam-based material with elastic characteristics, wherein the plurality of coils are located underneath the first planar element.

12. The system of claim 8, wherein the current generator generates and transmits an alternating current to the plurality of coils of the mat.

13. The system of claim 8, wherein the current generator generates and transmits a direct current to the plurality of coils of the mat.

14. A system for treating Alzheimer's disease in a patient, comprising:
    a) a magnetometer configured for measuring a directional component of a local magnetic field located in a vicinity of the patient's head, thereby producing a measurement B;
    b) a mat configured such that the patient may rest his head on said mat, the mat comprising a plurality of coils that, when activated, produce a uniform magnetic field emanating perpendicularly to a plane of the mat;
    c) a current generator coupled to the mat and configured for generating and transmitting a current to the plurality of coils of the mat; and
    d) a computing system coupled to the magnetometer and the current generator, the computing system configured for:
        1) receiving the measurement B from the magnetometer;
        2) calculating a frequency f of a current necessary for the plurality of coils of the mat to produce ion cyclotron resonance (ICR) of amyloid beta, wherein the following formula is used to calculate said frequency f:

$f = (1/2\pi)(qB/m)$, where $q/m$ is a charge to mass ratio of amyloid beta;

3) generating a current with the frequency f, and transmitting said current to the plurality of coils of the mat.

15. The system of claim 14, wherein the magnetometer is a vector magnetometer.

16. The system of claim 14, wherein the magnetometer is a total field magnetometer.

17. The system of claim 14, wherein the mat comprises a first planar element including a foam-based material with elastic characteristics, wherein the plurality of coils are located underneath the first planar element.

18. The system of claim 14, wherein the current generator generates and transmits an alternating current to the plurality of coils of the mat.

19. The system of claim 14, wherein the current generator generates and transmits a direct current to the plurality of coils of the mat.

\* \* \* \* \*